(12) United States Patent
Zhou

(10) Patent No.: US 10,152,027 B2
(45) Date of Patent: Dec. 11, 2018

(54) SMART WATCHES AND ASSOCIATED SYSTEMS AND METHODS FOR LOCK-SCREEN MANAGEMENT THEREOF

(71) Applicant: Huizhou TCL Mobile Communication Co., Ltd, Huizhou, Guangdong (CN)

(72) Inventor: Libin Zhou, Huizhou (CN)

(73) Assignee: HUIZHOU TCL MOBILE COMMUNICATION CO., LTD., Huizhou, Guangdong Province (CN)

( * ) Notice: Subject to any disclaimer, the term of this patent is extended or adjusted under 35 U.S.C. 154(b) by 35 days.

(21) Appl. No.: 15/328,396

(22) PCT Filed: Jun. 24, 2016

(86) PCT No.: PCT/CN2016/087053
§ 371 (c)(1),
(2) Date: Jan. 23, 2017

(87) PCT Pub. No.: WO2017/059698
PCT Pub. Date: Apr. 13, 2017

(65) Prior Publication Data
US 2017/0269556 A1    Sep. 21, 2017

(30) Foreign Application Priority Data
Oct. 9, 2015   (CN) .......................... 2015 1 0649440

(51) Int. Cl.
*G04G 9/00* (2006.01)
*A61B 5/024* (2006.01)
(Continued)

(52) U.S. Cl.
CPC ....... *G04G 9/0005* (2013.01); *A61B 5/02438* (2013.01); *A61B 5/117* (2013.01);
(Continued)

(58) Field of Classification Search
CPC . G04G 9/0005; A61B 5/002438; A61B 5/117; A61B 5/681
(Continued)

(56) References Cited

U.S. PATENT DOCUMENTS

2016/0357154 A1\* 12/2016 Shim .................... G06F 3/0346
2017/0134474 A1\* 5/2017 Gao ........................ H04L 67/04
(Continued)

FOREIGN PATENT DOCUMENTS

CN           103399483 A       11/2013
CN           103536279 A        1/2014
(Continued)

OTHER PUBLICATIONS

International Search Report on corresponding PCT application (PCT/CN2016/087053) from International Searching Authority (CN) dated Sep. 27, 2016.

*Primary Examiner* — Allen T Cao
(74) *Attorney, Agent, or Firm* — Cheng-Ju Chiang

(57) ABSTRACT

Smart watches and associated systems and methods thereof for lock-screen management are disclosed. A smart watch includes a heart rate sensor, and a method for lock-screen management of the smart watch includes: reading, by the heart rate sensor, a heart rate; determining based on the heart rate whether the smart watch has been taken off by the user, and if yes, stopping the heart rate sensor from working and entering by the smart watch a password-lock-screen mode. Thus, using the method according to the present disclosure can improve the information security on the smart watch.

20 Claims, 2 Drawing Sheets

(51) Int. Cl.
*A61B 5/117* (2016.01)
*A61B 5/00* (2006.01)
*G04G 9/08* (2006.01)
*G04G 21/02* (2010.01)
*G04C 3/00* (2006.01)

(52) U.S. Cl.
CPC ............. *A61B 5/681* (2013.01); *G04C 3/001* (2013.01); *G04G 9/087* (2013.01); *G04G 21/025* (2013.01)

(58) Field of Classification Search
USPC .................................................. 340/5.5–5.55
See application file for complete search history.

(56) References Cited

U.S. PATENT DOCUMENTS

| | | | | |
|---|---|---|---|---|
| 2017/0147988 | A1* | 5/2017 | Shin | G06Q 10/1095 |
| 2017/0220751 | A1* | 8/2017 | Davis | A61B 5/0015 |
| 2017/0357215 | A1* | 12/2017 | Shim | G06F 1/163 |

FOREIGN PATENT DOCUMENTS

| | | |
|---|---|---|
| CN | 104298352 A | 1/2015 |
| KR | 100610242 B1 | 8/2006 |

* cited by examiner

SMART WATCHES AND ASSOCIATED SYSTEMS AND METHODS FOR LOCK-SCREEN MANAGEMENT THEREOF

CROSS-REFERENCE TO RELATED APPLICATIONS

The present application is a 35 U.S.C. § 371 National Phase conversion of International (PCT) Patent Application No. PCT/CN2016/087053 filed Jun. 24, 2016, which claims foreign priority of Chinese Patent Application No. 201510649440.4, filed on Oct. 9, 2015 in the State Intellectual Property Office of China, the contents of all of which are hereby incorporated by reference.

TECHNICAL FIELD

Embodiments of the present disclosure generally relate to mobile terminals, and in particular to smart watches and associated systems and methods for lock-screen management thereof.

BACKGROUND

Wearable devices have now gained increasingly popularity and has brought huge convenience to people's daily lives. In particular, smart watches have developed rapidly. In addition to the timekeeping function, smart watches can also be used to make phone calls and for fast payments.

However, the security of user information on smart watches has become increasingly important as the development continues. As such, how to ensure users a smooth operating experience while protecting the information security has become a subject of intense research. Current smart watches can only be triggered manually to enter the password-lock-screen mode. That is, after unclasped, to prevent others from entering the main interface to use the smart watch functions, the smart watch needs to be locked with a password. So, if the wearer forgets to lock the screen of the smart watch, which is then unfortunately stolen, then serious information security issues may arise, which may impact the security of bank accounts after the introduction of payment functions to the smart watch.

SUMMARY

The present disclosure provides smart watches and associated systems and methods thereof for lock-screen management to address the information security issues of existing smart watches.

A method for lock-screen management of a smart watch that comprises a heart rate sensor is provided, the method comprising: reading, by the heart rate sensor, a heart rate; determining whether the heart rate remains zero within a predetermined period of time, and if yes, determining the smart watch is unclasped by the user; if the smart watch is unclasped, stopping the heart rate sensor from working, and entering, by the smart watch, a password-lock-screen mode; and otherwise if the smart watch is not unclasped by the user, then remaining, by the smart watch, unlocked or in a password-free-lock mode.

The method may further comprise, after the smart watch enters the password-lock-screen mode: entering, by the smart watch, a password input interface; and inputting a password to unlock the smart watch.

Inputting the password to unlock the smart watch may comprise: Inputting a pattern password or numeric password to unlock the smart watch.

The predetermined period of time may lie in range of 5 s-30 s.

The heart rate sensor may be a photoelectric heart rate sensor.

Reading by the heart rate sensor the heart rate may comprise: reading, by the heart rate sensor, the heart rate with a preset period.

The preset period may lie in range of 0.01 s-0.5 s.

A system for lock-screen management of a smart watch that comprises a heart rate sensor is provided, the system comprising: a determination module configured to determine, based on a heart rate read by the heart rate sensor, whether the smart watch is unclasped by the user, thus obtaining a determination result; a screen-lock module configured to have the smart watch enter a password-lock-screen mode when the determination result is yes; and the heart rate sensor configured to stop working when the determination result is yes.

The screen-lock module may be further configured to provide a password input interface on the smart watch and receive an input password to unlock the smart watch, after the smart watch enters the password-lock-screen mode.

The password may comprise a pattern password or numeric password.

The screen-lock module may further be configured to have the smart watch remain unlocked or remain in a password-free-lock mode when the determination result is no.

The determination module may specifically be configured to determine whether the heart rate remains zero within a predetermined period of time, and if yes, determine the smart watch is unclasped by the user, and the determination result will be yes.

The predetermined period of time may lie in a range of 5 s-30 s.

The heart rate sensor may be a photoelectric heart rate sensor.

The heart rate sensor may be configured to read the heart rate with a preset period.

The preset period may lie in a range of 0.01 s-0.5 s.

There is further provided a smart watch that comprises a heart rate sensor and a processor, the heart rate sensor being configured to read a heart rate, and the processor being configured to determine, based on the heart rate, whether the smart watch is unclasped, and if yes, stop the heart rate sensor from working and have the smart watch enter a password-lock-screen mode.

If the processor determines the smart watch is not unclasped by the user, then the smart watch may remain unlocked or in a password-free-lock mode.

The processor may be configured to determine whether the heart rate remains zero within a predetermined period of time, and if yes, determine the smart watch is unclasped by the user.

The processor may be configured to control the heart rate sensor to read the heart rate with a preset period.

According to the method for lock-screen management of a smart watch equipped with a heart rate sensor that is disclosed by the disclosure, the heart rate sensor may read a heart rate, which can be based on to determine whether the smart watch has been unclasped from the user. If the smart watch has been removed, then the heart rate sensor may stop working and the smart watch may enter a password-lock-screen mode. Therefore, the smart watch can automatically enter the password-lock-screen mode when it is taken off, so that the user needs not to lock the screen manually, thus improving the user experience and avoiding the security problems caused by the user forgetting to lock the screen.

DETAILED DESCRIPTION

Figure 1:
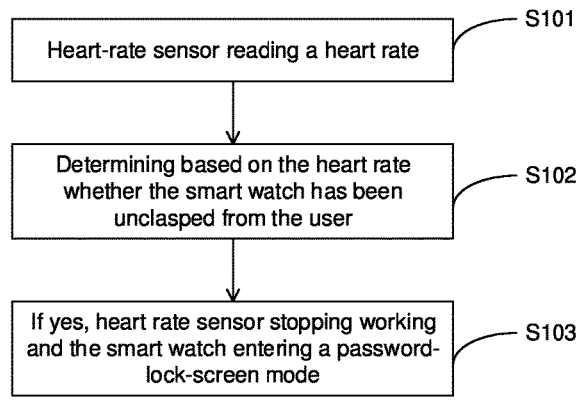
FIG. 1 is a flowchart illustrating a first embodiment of a method for lock-screen management of a smart watch according to the disclosure.

Referring to FIG. 1, a flowchart illustrating a first embodiment of a method for lock-screen management of a smart watch is depicted. The method is based on a smart watch embedded with a heart rate sensor and may comprise the following blocks.

In S101, the heart rate sensor may read a heart rate.

With the smart watch worn around the user's wrist, the heart rate sensor built in the smart watch can read the user's heart rate to obtain a heart rate reading.

The heart rate sensor can be divided into two major types including electrode heart rate sensor and photoelectric heart rate sensor. While the electrode heart rate sensor can provide a comparatively higher detection precision, it requires detecting two parts of the body at the same time, hence difficult to achieve continuous detection. Rather, if the smart watch is mainly used for health care, where more accurate data may be needed, then the electrode heart rate sensor can be applied.

Most current smart watches use the photoelectric heart rate sensor which comprises a detector and a light source, where the light source can cast light upon the subcutaneous capillaries, so that when the heart pumps fresh blood through the capillaries, the brightness of the capillaries may undergo wavy periodic changes, thereby the detector can detect this regular change to derive the heart rate.

In the present embodiment the photoelectric heart rate sensor is applied, and the detection of the heart rate requires the cooperation of the light source and the detector. The light source can remain lit up, while the detector can perform detection regularly. However, in this case, the light source may consume a relatively large amount of power, and hence not conducive to the battery life of the smart watch. Or in another case, the light source may illuminate with a certain period and, correspondingly, the detector can perform detection only when the light source lights up, thus reducing the power consumption to a certain extent. In both cases the period mentioned may be the heart rate detection period T1, and may range from 0.01 s-0.5 s. Because the normal resting heart rate of the human body is typically 60-100 beats/minute, to ensure the detection precision, the maximum of the detection period T1 may be set to 0.5 s. Typically, the smaller the period, the higher the detection precision, but if the period is too small, it is likely to cause excessive power consumption. Therefore, considering the energy-efficiency, the minimum value of the detection period T1 may be set to 0.01 s.

In S102, the heart rate may be based on to determine whether the smart watch has been unclasped by the user.

In particular, the heart rate is used to determine whether the smart watch is taken off by the user. When worn by the user, the heart rate sensor can detect the heart rate. Otherwise, if removed, the heart rate sensor would not be able to detect the heart rate. Namely, the heart rate sensor may determine whether the heart rate changes from being present to not being present. If yes, then it means the smart watch may be taken off. Otherwise, if the heart rate is still present, then it may indicate the smart watch is not removed.

However, the smart watch would not be attached to the hand all the time. For example, there may be occasions when the smart watch is indeed worn on the wrist but the heart rate is unable to be detected. Thus, in S102 the condition for determining that the smart watch has been removed may be as follows: the heart rate changes from being present to non-being present, and cannot be detected for a continuous period of time T2. Regarding the value of T2, if it is relatively too small, then it may easily lead to erroneous locking of the screen. In particular, if the smart watch is worn too loosely around the wrist so that the heart rate cannot be detected for a period of time, then the screen may be locked automatically, leading to poor user experience. On the other hand, if the value is relatively too large, then the screen may be unable to lock in time, which may still be likely to cause security problems. Therefore, in the present embodiment, T2 ranges from 5 s-30 s.

More specifically, if the detection period T1 for the heart rate is 0.5 s, and the heart rate changes from being present to non-being present, and the heart rate cannot be detected for a continuous period of 30 s, e.g., T2=30 s, then the smart watch may be determined as unclasped. In another example, if the heart rate detection period T1 is 0.01 s, and the heart rate changes from being present to non-being present, and the heart rate cannot be detected for a continuous period of 5 s, e.g., T2=5 s, then the smart watch may be determined as unclasped. Typically, the heart rate detection period T1 may be set to 0.1 s, which can not only ensure the detection precision, but also save the power, thus achieving a balance between the two; meanwhile, the T2 may be set to 10 s, which means that if the heart rate changes from being present to non-being present and remains undetectable for a continuous period of 10 s, then the smart watch may be determined as taken off. It is worth mentioning that the setting of 10 s is suitable for most people's usage. Certainly, personalized settings of T1 and T2 can also be built in the smart watch, that is, the user may be allowed options to set T1 and T2 according to his own usage.

The smart watch implementing the present embodiment may not only have the lock-screen management function according to the disclosure, but also other functions including motion analysis, sleep quality monitoring, health monitoring, etc. In addition, since the photoelectric heart rate sensor has insufficient detection precision, in the present embodiment, a dedicated circuit may be required to correct and adjust the heart rate readings.

If in S102, it is determined that the smart watch is unclasped by the user, then the method may proceed to S103.

In S103, the heart rate sensor may stop working and the smart watch may enter a password-lock-screen mode.

After the smart watch has been unclasped so that the heart rate sensor would be unable to detect the heart rate, the heart rate sensor may automatically stop working in order to reduce the power consumption. Further, the smart watch may enter the password-lock-screen mode, and the screen of the smart watch may dim, so then if the user desires to enter the main interface, a password may need to be entered.

To ensure the basic functions of the smart watch, for example, if the user only desires to know the time through the smart watch, in the present embodiment, after the smart watch enters the password-lock-screen mode, the screen would only display the time, and the user may need to enter the password to perform other operations.

Figure 2:
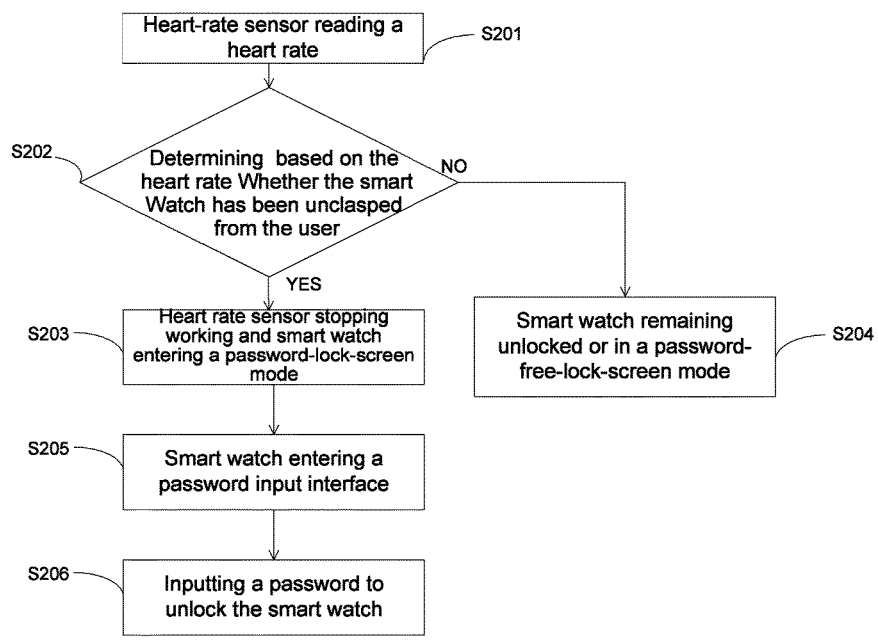
FIG. 2 is a flowchart illustrating a second embodiment of a method for lock-screen management of a smart watch according to the disclosure.

Referring now to FIG. 2, a flowchart illustrating a second embodiment of a method for lock-screen management of a smart watch is depicted. In this embodiment the smart watch may comprise a heart rate sensor and the method may comprise the following blocks.

In S201, the heart rate sensor may read a heart rate.

In S202, the heart rate may be based on to determine whether the smart watch has been unclasped by the user.

If the determination is yes, then the method may proceed to S203, otherwise to S204.

In S203, the heart rate sensor may stop working and the smart watch may enter a password-lock-screen mode.

The blocks S201-S203 in the present embodiment are similar to the blocks S101-S103 in the first embodiment, and hence will not be detailed again.

In S204, the smart watch may remain unlocked or in a password-free-lock mode.

If determining the smart watch is not unclasped from the user, e.g., it is continuously worn on the user's wrist, then the smart watch may stay in the unlocked state, meaning all possible operations are available without the need to enter a password. Or, the smart watch may remain in the password-free lock screen state, in which the wearer can touch the screen or press a certain physical button to enter the main interface of the smart watch, hence no password is required.

In S205, the smart watch may enter a password input interface.

After the smart watch is taken off from the user and then enters the lock screen mode in S203, if the user desires to enter the main interface of the smart watch to perform an operation, then the password input interface may first be entered, following which the method may proceed to S206.

In S206, a password may be inputted to unlock the smart watch.

In the present embodiment two types of password modes can be applied, including the pattern password and the numeric password. The pattern password or the pattern lock, may comprise 9 dots arranged as a 3×3 grid. For example, the user can select any four from among the 9 dots and connect the four dots in any possible way to form a password pattern. However, considering the dial is generally small, the numeric password mode may typically be deployed.

Figure 3:
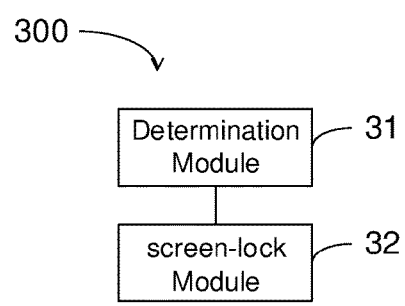
FIG. 3 is a block diagram illustrating a first embodiment of a system for lock-screen management of a smart watch according to the disclosure.

Referring now to FIG. 3, a block diagram illustrating a first embodiment of a system for lock-screen management of a smart watch according to the disclosure is depicted. The smart watch may comprise a heart rate sensor. The system 300 may comprise a determination module 31 and a screen-lock module 32.

The determination module 31 may be configured to determine whether the smart watch has been unclasped by the user based on a heart rate reading from the heart rate sensor, thus obtaining a determination result.

The screen-lock module 32 may be configured to read the determination result and have the smart watch enter a password-lock-screen mode when the determination result is yes. Meanwhile, the heart rate sensor may also stop working if the determination result is yes.

Otherwise, if the determination result is no, the screen-lock module 32 may be configured to have the smart watch remain unlocked or remain in a password-free-lock mode.

The screen-lock module 32 may further be configured to provide a password input interface on the smart watch and receive an input password by which the smart watch may be unlocked, after the smart watch enters the password-lock-screen mode. The password may be a pattern password or numeric password.

Various modules of the present embodiment may be configured to carry out the corresponding steps of the second embodiment of the method for lock screen management, so the specific work process of each module will not be described again in detail herein.

Figure 4:
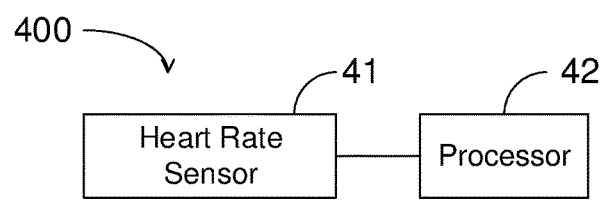
FIG. 4 is a block diagram illustrating a first embodiment of a smart watch according to the disclosure.

Referring now to FIG. 4, a block diagram illustrating a first embodiment of a smart watch according to the disclosure is depicted. The smart watch may 400 may comprise a heart rate sensor 41 and a processor 42.

The heart rate sensor 41 may be configured to read a heart rate, and the processor 42 may be configured to determine based on the heart rate sensor whether the smart watch 400 has been unclasped, and if yes, stop the heart rate sensor 41 from working and have the smart watch 400 enter a password-lock-screen mode.

The processor 42 in the present embodiment may be configured to accomplish various blocks of the method for lock-screen management of a smart watch, so the specific work process of the processor 42 will not described in detail again.

Note that, the processor 42 can be built inside the dial, while the heart rate sensor 41 may be disposed at a side of the dial of the smart watch 400 that is close to the user's skin. Since the dial comes in contact with a relatively large skin area, disposing the heart rate sensor 41 on the dial may lead to fewer errors in heart rate detection.

If the detected heart rate reading needs to be analyzed and processed, then a correction circuit (not shown) can further be added in the smart watch 400 and specifically coupled to the processor 42. The correction circuit may be disposed inside the dial or strip and used to adjust and correct the detected heart rate reading.

According to the method for lock-screen management of a smart watch equipped with a heart rate sensor that is disclosed by the disclosure, the heart rate sensor may read a heart rate, which can be based on to determine whether the smart watch has been unclasped by the user. If the smart watch has been unclasped, then the heart rate sensor may stop working and the smart watch may enter a password-lock-screen mode. Therefore, the smart watch can automatically enter the password-lock-screen mode when it is taken off, so that the user needs not to lock the screen manually, thus improving the user experience and avoiding the security problems caused by the user forgetting to lock the screen.

Furthermore, it is apparent to those skilled in the art that the present disclosure also provides a system for lock-screen management of a smart watch, the system comprising a non-transitory program storage medium and one or more processors. The non-transitory program storage medium stores a plurality of programs executable by the processor(s) to perform the methods as described above. Furthermore, it is apparent to those skilled in the art that various units or modules 31 and 32, as shown in FIG. 3, can be software modules or software units. In another aspect, it is well-known that various software modules or software units can be inherently stored in the non-transitory program storage medium and executed by the processor(s).

The above description merely illustrates some exemplary embodiments of the disclosure, but is not intended to limit the scope of the disclosure. Any equivalent structure or flow transformations made to the disclosure, or any direct or indirect applications of the disclosure on any other related fields, shall all be covered in the scope of the disclosure.

What is claimed is:

1. A method for lock-screen management of a smart watch that comprises a heart rate sensor, the method comprising:
   reading, by the heart rate sensor, a heart rate;
   judging whether the heart rate remains zero within a predetermined period of time; wherein
   when the heart rate remains zero within the predetermined period of time, it is determined that the smart watch has been removed from a wrist of a user, and the smart watch stopping the heart rate sensor from working and entering a password-lock-screen mode; and
   when the heart rate does not remain zero within the predetermined period of time, it is determined that the smart watch is not removed from the wrist of the user, and the smart watch remaining unlocked or in a password-free-lock mode.

2. The method according to claim 1, further comprising, after the smart watch entering the password-lock-screen mode:
   entering a password input interface of the smart watch; and
   inputting a password to unlock the smart watch.

3. The method according to claim 2, wherein inputting the password to unlock the smart watch comprises:
   inputting a pattern password or numeric password to unlock the smart watch.

4. The method according to claim 1, wherein the predetermined period of time lies in a range of 5 seconds to 30 seconds.

5. The method according to claim 1, wherein the heart rate sensor is a photoelectric heart rate sensor.

6. The method according to claim 5, wherein the reading, by the heart rate sensor, the heart rate comprises:
   reading, by the heart rate sensor, the heart rate with a preset period.

7. The method according to claim 6, wherein the preset period lies in a range of 0.01 seconds to 0.5 seconds.

8. A system for lock-screen management of a smart watch that comprises a heart rate sensor, the system comprising a memory storing a plurality of programs and one or more processors that execute one or more operations for the plurality of programs, the plurality of programs comprising:
   a determination module configured to determine whether the smart watch has been removed from a wrist of a user based on a heart rate read by the heart rate sensor; and
   a screen-lock module configured to control the smart watch to enter a password-lock-screen mode when it is determined that the smart watch has been removed from the wrist of the user;
   wherein the heart rate sensor stops working when it is determined that the smart watch has been removed from the wrist of the user.

9. The system according to claim 8, wherein the screen-lock module is further configured to provide a password input interface of the smart watch and receive an input password to unlock the smart watch, after the smart watch has entered the password-lock-screen mode.

10. The system according to claim 9, wherein the password comprises a pattern password or numeric password.

11. The system according to claim 8, wherein the screen-lock module is further configured to have the smart watch remain unlocked or in a password-free-lock mode when it is determined that the smart watch is not removed from the wrist of the user.

12. The system according to claim 8, wherein the determination module is further configured to judge whether the heart rate remains zero within a predetermined period of time; when the heart rate remains zero within the predetermined period of time, it is determined that the smart watch has been removed from the wrist of the user.

13. The system according to claim 12, wherein the predetermined period of time lies in a range of 5 seconds to 30 seconds.

14. The system according to claim 8, wherein the heart rate sensor is a photoelectric heart rate sensor.

15. The system according to claim 14, wherein the heart rate sensor is configured to read the heart rate with a preset period.

16. The system according to claim 15, wherein the preset period lies in a range of 0.01 seconds to 0.5 seconds.

17. A smart watch, comprising a heart rate sensor and a processor, wherein:
   the heart rate sensor is configured to read a heart rate; and
   the processor is configured to:
   determine whether the smart watch has been removed from a wrist of a user based on the heart rate read by the heart rate sensor; and
   when it is determined that the smart watch has been removed from the wrist of the user, stop the heart rate sensor from working and control the smart watch to enter a password-lock-screen mode.

18. The smart watch according to claim 17, wherein if the processor determines the smart watch is not removed from the wrist of the user, the smart watch remains unlocked or in a password-free-lock mode.

19. The smart watch according to claim 17, wherein the processor is configured to judge whether the heart rate remains zero within a predetermined period of time; when the heart rate remains zero within the predetermined period of time, it is determined that the smart watch has been removed from the wrist of the user.

20. The smart watch according to claim 17, wherein the processor is configured to control the heart rate sensor to read the heart rate with a preset period.

* * * * *